US007137986B2

(12) United States Patent
Troxell et al.

(10) Patent No.: US 7,137,986 B2
(45) Date of Patent: Nov. 21, 2006

(54) TRANSCONNECTOR FOR COUPLING SPINAL RODS

(75) Inventors: Thomas N. Troxell, Pottstown, PA (US); G. Kris Kumar, West Chester, PA (US); Barclay R. Davis, Downingtown, PA (US); Thomas J. Runco, Wayne, PA (US)

(73) Assignee: Synthes (U.S.A.), West Chester, PA (US)

( * ) Notice: Subject to any disclaimer, the term of this patent is extended or adjusted under 35 U.S.C. 154(b) by 227 days.

(21) Appl. No.: 10/801,883

(22) Filed: Mar. 15, 2004

(65) Prior Publication Data
US 2004/0176765 A1 Sep. 9, 2004

Related U.S. Application Data

(63) Continuation of application No. 09/927,350, filed on Aug. 13, 2001, now Pat. No. 6,736,817, which is a continuation of application No. 09/466,725, filed on Dec. 17, 1999, now Pat. No. 6,283,967.

(51) Int. Cl.
*A61B 17/56* (2006.01)
*A61B 17/58* (2006.01)
*A61B 2/30* (2006.01)

(52) U.S. Cl. .............................. 606/61; 606/60; 606/72; 606/73; 606/86

(58) Field of Classification Search ................. 606/60, 606/61, 72, 73, 86, 103, 53
See application file for complete search history.

(56) References Cited

U.S. PATENT DOCUMENTS

| | | | | |
|---|---|---|---|---|
| 4,257,409 A | 3/1981 | Bacal et al. | ................... | 128/69 |
| 4,361,141 A | 11/1982 | Tanner | .................... | 128/69 |
| 4,369,770 A | 1/1983 | Bacal et al. | ................... | 128/69 |
| 4,433,677 A | 2/1984 | Ulrich et al. | .................. | 128/69 |
| 4,611,582 A | 9/1986 | Duff | ............................. | 128/69 |
| 4,815,453 A | 3/1989 | Cotrel | ......................... | 128/69 |
| 4,955,885 A | 9/1990 | Meyers | ........................ | 606/53 |
| 4,998,936 A | 3/1991 | Mehdian | ...................... | 606/61 |
| 5,005,562 A | 4/1991 | Cotrel | ......................... | 128/69 |

(Continued)

FOREIGN PATENT DOCUMENTS

DE 32 19 575 A1 12/1983

(Continued)

*Primary Examiner*—Eduardo C. Robert
*Assistant Examiner*—John Kim
(74) *Attorney, Agent, or Firm*—Jones Day

(57) ABSTRACT

The present invention is directed to a transconnector for coupling first and second spinal fixation rods or other elongate fixation elements. The transconnector includes a male member, a female member, and a locking member. The male member has a body with a linking element (such as a hook) associated with the lateral end for receiving one of the fixation elements, and a projection on the medial end. The projection includes a recess defined by lateral and medial walls. The female member has a body with a linking element associated with the lateral end for receiving the other fixation element, and a cavity with an opening on the medial end for receiving a portion of the male member projection. The locking member secures the position and orientation of the male member projection portion in the cavity in order to accommodate different separation distances and orientations between the first and second fixation elements. The locking member cooperates with the medial wall of the recess of the projection to prevent uncoupling of the male and female members. The male member may be made as a two component assembly in which the two components can rotate relative to one another for accommodating rod convergence or divergence.

93 Claims, 6 Drawing Sheets

U.S. PATENT DOCUMENTS

| | | | |
|---|---|---|---|
| 5,010,879 A | 4/1991 | Moriya et al. | 128/69 |
| 5,084,049 A | 1/1992 | Asher et al. | 606/61 |
| 5,133,716 A | 7/1992 | Plaza | 606/61 |
| 5,147,360 A | 9/1992 | Dubousset | 606/61 |
| 5,154,718 A | 10/1992 | Cozad et al. | 606/61 |
| 5,261,907 A | 11/1993 | Vignaud et al. | 606/60 |
| 5,275,600 A | 1/1994 | Allard et al. | 606/61 |
| 5,312,405 A | 5/1994 | Korotko et al. | 606/61 |
| 5,330,473 A | 7/1994 | Howland | 606/61 |
| 5,334,203 A | 8/1994 | Wagner | 606/61 |
| D353,003 S | 11/1994 | Dinello | D24/155 |
| 5,366,455 A | 11/1994 | Dove et al. | 606/61 |
| 5,395,370 A | 3/1995 | Muller et al. | 606/61 |
| 5,397,363 A | 3/1995 | Gelbard | 623/17 |
| 5,423,818 A | 6/1995 | Van Hoeck et al. | 606/61 |
| 5,437,671 A | 8/1995 | Lozier et al. | 606/61 |
| 5,439,463 A | 8/1995 | Lin | 606/61 |
| 5,476,462 A | 12/1995 | Allard et al. | 606/60 |
| 5,487,742 A * | 1/1996 | Cotrel | 606/61 |
| 5,498,263 A | 3/1996 | DiNello et al. | 606/61 |
| 5,507,746 A | 4/1996 | Lin | 606/61 |
| 5,522,816 A | 6/1996 | Dinello et al. | 606/61 |
| 5,527,314 A | 6/1996 | Brumfield et al. | 606/61 |
| 5,531,747 A | 7/1996 | Ray | 606/61 |
| 5,534,002 A | 7/1996 | Brumfield et al. | 606/61 |
| 5,549,607 A | 8/1996 | Olson et al. | 606/61 |
| 5,569,246 A | 10/1996 | Ojima et al. | 606/61 |
| 5,601,552 A | 2/1997 | Cotrel | 606/61 |
| 5,620,444 A | 4/1997 | Assaker | 606/61 |
| 5,624,442 A | 4/1997 | Mellinger et al. | 606/61 |
| 5,630,816 A | 5/1997 | Kambin | 606/61 |
| 5,651,789 A | 7/1997 | Cotrel | 606/61 |
| 5,667,506 A | 9/1997 | Sutterlin | 606/61 |
| 5,667,507 A | 9/1997 | Corin et al. | 606/61 |
| 5,669,910 A | 9/1997 | Korhonen et al. | 606/61 |
| 5,676,665 A | 10/1997 | Bryan | 606/61 |
| 5,681,312 A | 10/1997 | Yuan et al. | 606/61 |
| 5,688,272 A | 11/1997 | Montague et al. | 606/61 |
| 5,693,053 A | 12/1997 | Estes | 606/61 |
| 5,707,372 A | 1/1998 | Errico et al. | 606/61 |
| 5,709,684 A | 1/1998 | Errico et al. | 606/61 |
| 5,716,355 A | 2/1998 | Jackson et al. | 606/61 |
| 5,752,955 A | 5/1998 | Errico | 606/61 |
| 5,885,284 A | 3/1999 | Errico | 606/61 |
| 5,928,231 A | 7/1999 | Klein et al. | 606/60 |
| 5,947,966 A | 9/1999 | Dewry | 606/61 |
| 5,980,523 A | 11/1999 | Jackson | 606/61 |
| 5,984,923 A | 11/1999 | Breard | 606/61 |
| 5,989,251 A | 11/1999 | Nichols | 606/61 |
| 6,083,226 A | 7/2000 | Fiz | 606/61 |
| 6,096,039 A | 8/2000 | Stoltenberg et al. | 606/61 |
| 6,110,173 A | 8/2000 | Thomas, Jr. | 606/61 |
| 6,113,600 A | 9/2000 | Drummond et al. | 606/61 |
| 6,136,000 A | 10/2000 | Louis et al. | 606/61 |
| 6,136,003 A | 10/2000 | Hoeck et al. | 606/61 |
| 6,171,311 B1 | 1/2001 | Richelsoph | 606/61 |
| 6,217,578 B1 | 4/2001 | Crozet et al. | 606/61 |
| 6,234,705 B1 | 5/2001 | Troxell | 403/237 |
| 6,238,396 B1 | 5/2001 | Lombardo | 606/61 |
| 6,261,288 B1 | 7/2001 | Jackson | 606/61 |
| 6,264,658 B1 | 7/2001 | Lee et al. | 606/61 |
| 6,283,967 B1 | 9/2001 | Troxell et al. | 606/61 |
| 6,302,882 B1 | 10/2001 | Lin et al. | 606/61 |
| 6,306,137 B1 | 10/2001 | Troxell | 606/61 |
| 6,328,741 B1 | 12/2001 | Richelsoph | 606/61 |
| 6,355,038 B1 | 3/2002 | Pisharodi | 606/61 |
| 6,402,751 B1 | 6/2002 | Hoeck et al. | 606/61 |
| 6,413,258 B1 | 7/2002 | Bernhardt, Jr. | 606/61 |
| 6,432,108 B1 | 8/2002 | Burgess et al. | 606/61 |
| 6,524,310 B1 | 2/2003 | Lombardo et al. | 606/61 |
| 6,551,318 B1 | 4/2003 | Stahurski | 606/61 |
| 6,554,832 B1 | 4/2003 | Shluzas | 606/61 |
| 6,562,040 B1 | 5/2003 | Wagner | 606/61 |
| 6,589,243 B1 | 7/2003 | Viart et al. | 606/61 |
| 6,602,253 B1 | 8/2003 | Richelsoph et al. | 606/61 |
| 6,602,254 B1 | 8/2003 | Gertzbein et al. | 606/61 |
| 6,616,668 B1 | 9/2003 | Altarac et al. | 606/61 |
| 2001/0047171 A1 | 11/2001 | Troxell et al. | 606/61 |
| 2002/0052603 A1 | 5/2002 | Nichols et al. | 606/61 |
| 2002/0082599 A1 | 6/2002 | Crandall et al. | 606/61 |
| 2002/0138077 A1 | 9/2002 | Ferree | 606/61 |
| 2002/0143327 A1 | 10/2002 | Shluzas | 606/61 |
| 2002/0169448 A1 | 11/2002 | Vanacker | 606/61 |
| 2002/0169450 A1 | 11/2002 | Lange | 606/61 |
| 2002/0169451 A1 | 11/2002 | Yeh | 606/61 |
| 2003/0004512 A1 | 1/2003 | Farris et al. | 606/61 |
| 2003/0028192 A1 | 2/2003 | Schar et al. | 606/61 |
| 2003/0045874 A1 | 3/2003 | Thomas, Jr. | 606/61 |
| 2003/0050640 A1 | 3/2003 | Lee et al. | 606/61 |
| 2003/0083659 A1 | 5/2003 | Lin et al. | 606/61 |

FOREIGN PATENT DOCUMENTS

| | | |
|---|---|---|
| DE | 43 30 837 A1 | 9/1993 |
| EP | 0 811 357 A1 | 12/1997 |
| EP | 0 813 845 A1 | 12/1997 |
| EP | 0 953 316 A1 | 11/1999 |
| FR | 2 645 427 | 4/1989 |
| FR | 2 714 590 | 1/1994 |
| JP | 2002-355252 | 12/2002 |
| WO | WO 02/38061 | 5/2002 |

* cited by examiner

TRANSCONNECTOR FOR COUPLING SPINAL RODS

CROSS-REFERENCE TO RELATED APPLICATION

The present application is a continuation of U.S. patent application Ser. No. 09/927,350, filed Aug. 13, 2001 now U.S. Pat. No. 6,736,817 B1, which is a continuation of U.S. patent application Ser. No. 09/466,725, filed Dec. 17, 1999, now U.S. Pat. No. 6,283,967 B1, the entire content of which are expressly incorporated herein by reference thereto.

FIELD OF THE INVENTION

The present invention relates to a device for spinal fixation, and in particular to a transconnector for coupling spinal rods, plates, or other elongate members.

BACKGROUND OF THE INVENTION

It is often necessary to surgically treat spinal disorders such as scoliosis. Numerous systems for use in spinal correction and fixation have been disclosed. These systems usually include a pair of elongate members, typically either rods or plates, placed along the vertebral column. For the sake of simplicity, the term "rod" is used throughout to refer to any elongate member. Each rod is attached to the spine with various attachment devices. These attachment devices may include, but are not limited to, pedicle screws, plates, transverse process hooks, sublaminar hooks, pedicle hooks, and other similar devices.

It is also well known that the strength and stability of the dual rod assembly can be increased by coupling the two rods with a cross-brace or transconnector which extends substantially horizontal to the longitudinal axes of the rods across the spine. The simplest situation in which a transconnector could be used occurs when the two rods are geometrically aligned. Specifically, the two rods are parallel to each other, i.e. there is no rod convergence or divergence in the medial-lateral direction; the two rods have the same orientation with respect to the coronal plane (viewed in the anterior-posterior direction), i.e. the rods are coplanar from a lateral view; and the two rods are located a uniform distance from each other.

Due to a wide variety of factors, the two rods are rarely three dimensionally geometrically aligned in clinical situations. There are several ways to address the variations of geometrical alignment. First, one or both of the rods can be bent to accommodate the transconnector. However, any bending in either of the rods can adversely affect the fixation to the spine and comprise clinical outcome. Furthermore, the bending can also adversely affect the mechanical properties of the rods. The transconnector can also be bent so that the disturbance to the rod positioning is minimized. As is the case with bending of the rods, the mechanical properties of the transconnector could be compromised.

Transconnectors with some adjustability have been designed to adapt for variations from geometrical alignment. However, most are multi-piece systems that can be difficult to assemble and use in the surgical environment. U.S. Pat. No. 5,980,523 discloses a multi-piece transverse connector for spinal rods that can accommodate converging or diverging rods. However, accidental disassembly of the connector by the surgeon is possible. Even those that are one-piece designs do not allow for adjustments to compensate for all three modes in which there may be variation from geometrical alignment: convergence or divergence, non-coplanar rods, and variability in rod separation distances. For example, U.S. Pat. No. 5,947,966 discloses a device for linking adjacent spinal rods. In one embodiment, the device includes two members that are movable with respect to one another to accommodate different rod separation distances. A pin on one member engages a groove on the other member to provisionally couple the two members, thereby preventing a surgeon from separating the two members. Because the pin is sized to exactly fit the groove, no movement of the pin transverse to the longitudinal axis of the groove is possible. As a result, the device disclosed in the '966 patent cannot accommodate non-coplanar rods or adjust for rod convergence or divergence.

Thus, there exists a need for an improved transconnector for coupling spinal rods.

SUMMARY OF THE INVENTION

The present invention relates to a transconnector for coupling first and second elongate spinal fixation elements that have different three dimensional orientations. The transconnector includes a male member, a female member and a locking member and can be made of any suitable material such as titanium, a titanium alloy, or stainless steel. The male member comprises a body with lateral and medial ends, a linking element associated with the lateral end and being configured and dimensioned to receive one of the fixation elements, and a projection on the medial end. The projection includes a body with a recess defined by lateral and medial walls. The female member comprises a body with lateral and medial ends, a linking element associated with the lateral end and being configured and dimensioned to receive one of the fixation elements, and a cavity with an opening on the medial end which is configured and dimensioned to receive a portion of the male member projection. The locking member secures the position and orientation of the male member projection portion in the cavity in order to accommodate different separation distances and orientations between the first and second fixation elements. The locking member interacts with the medial wall of the recess to limit travel of the male member projection portion in the cavity, thereby preventing uncoupling of the male and female members.

Preferably, the locking member comprises a threaded hole in the body of the female member and a set screw threadably received in the threaded hole. The set screw has a first end for receiving a tool to turn the set screw and a second end contactable with the projection for pressing the projection against the cavity. The recess may have a width wider than a width of the second end of the set screw for the rotation of the projection in the cavity. In an exemplary embodiment, the projection has a substantially cylindrical shape with a first radius and the recess has a curved upper surface with a second radius. The first radius is larger than the second radius and the second end of the set screw extends into the recess to limit the rotation of the projection in the cavity. The set screw can be a threaded cylindrical body transitioning to a tip at the second end of the set screw.

The male member body may comprise a link terminal having a lateral end with the male member linking element, an intermediate link having a medial end with the projection of the male member and a lateral end engaging the medial end of the link terminal, and a locking element for securing the link terminal to the intermediate link. Preferably, the medial end of the link terminal includes a first textured surface and the lateral end of the intermediate link includes a second textured surface mating with the first textured surface. The first textured surface is rotatable with respect to the second textured surface for accommodating convergence or divergence between the first and second rods. An example of suitable first and second textured surfaces includes a radial or star-grind pattern.

The locking element preferably comprises a first hole through the medial end of the link terminal, a second hole through the lateral end of the intermediate link aligned with the first hole, and a cap screw insertable in the first and second holes. The cap screw may have a second end with a retaining ring for preventing removal of the cap screw from the second hole. The retaining ring may include a resilient member which flexes inward upon insertion of the cap screw through the second hole and flexes outward once the resilient member is past a collar in the second hole. Preferably, the resilient member includes an end of the cap screw with a lip and a plurality of slits.

If rods are used for the elongate fixation elements, then the male member linking element preferably comprises a hook and the female member linking element preferably comprises a hook. The lateral ends of the male and female members each may include a threaded hole and a clamping screw threadably received in the respective threaded hole for securing the fixation elements to the respective hook. The fixation elements are preferably clamped between a conical second body portion of the respective clamping screw and a region near the tip portion of the respective hook when the transconnector is secured to the fixation elements.

BRIEF DESCRIPTION OF THE DRAWINGS

Preferred features of the present invention are disclosed in the accompanying drawings, wherein similar reference characters denote similar elements throughout the several views, and wherein.

DETAILED DESCRIPTION OF THE PREFERRED EMBODIMENTS

Figure 1:
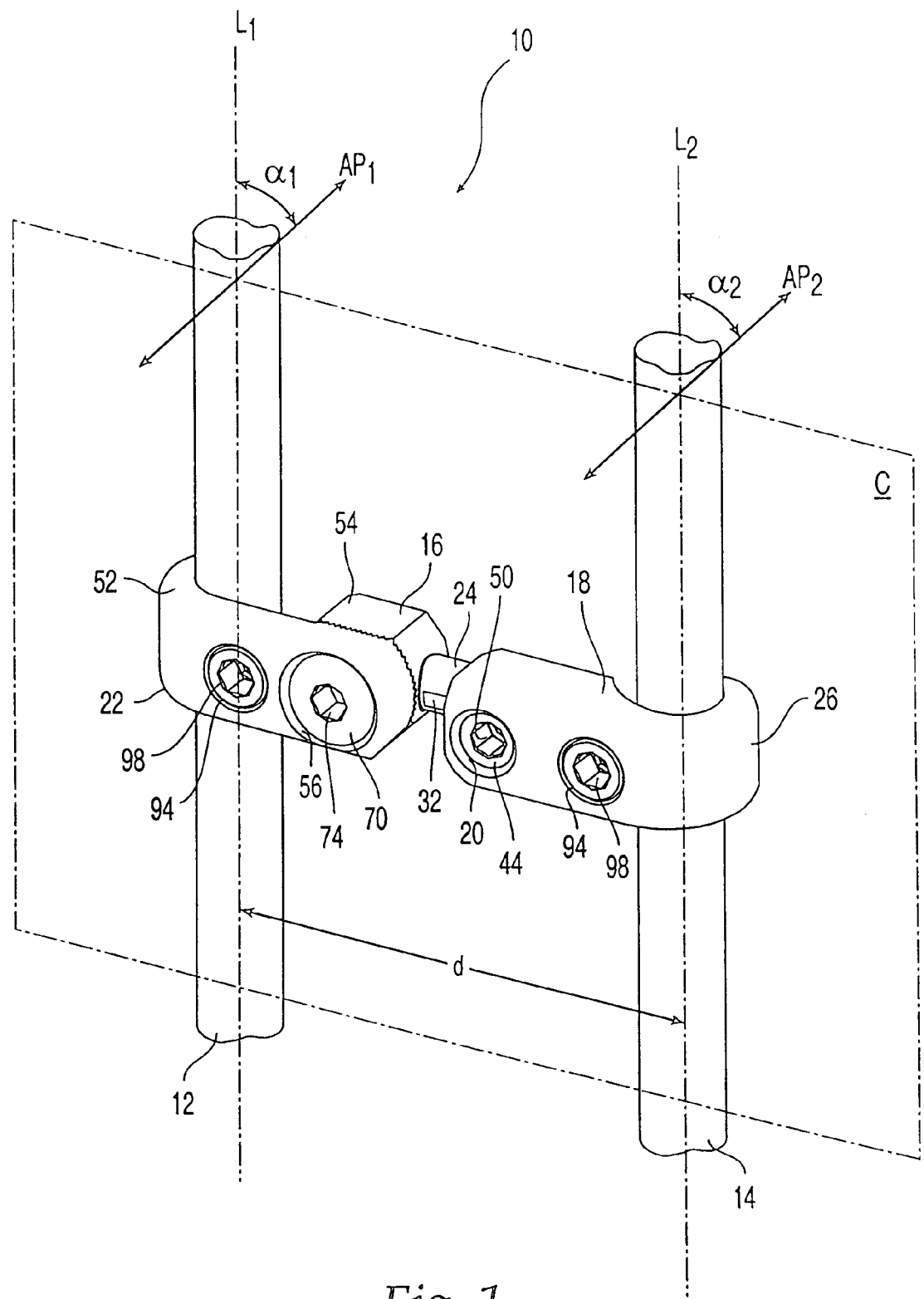
FIG. 1 shows a top perspective view of a transconnector according to the present invention with an elongate fixation element attached at each end.

FIG. 1 shows a transconnector 10 according to the present invention for coupling a first elongate spinal fixation element 12 to a second elongate spinal fixation element 14. Transconnector 10 can be made of any suitable material typically used in orthopaedic applications such as titanium, titanium alloy, or stainless steel. If transconnector 10 is made of a metallic material, preferably it is the same metallic material used for fixation elements 12, 14 to avoid galvanic (mixed-metal) corrosion. First and second fixation elements 12, 14 can be cylindrical rods, rectangular bars, plates, or any other device suitable for spinal fusion. In use, first fixation element 12 extends along one side of the vertebral column and second fixation element 14 extends along the other side of the vertebral column. A wide variety of attachment devices such as hooks, screws, and clamps, can be used to attach first and second fixation elements 12, 14 to the spine.

Figure 6:
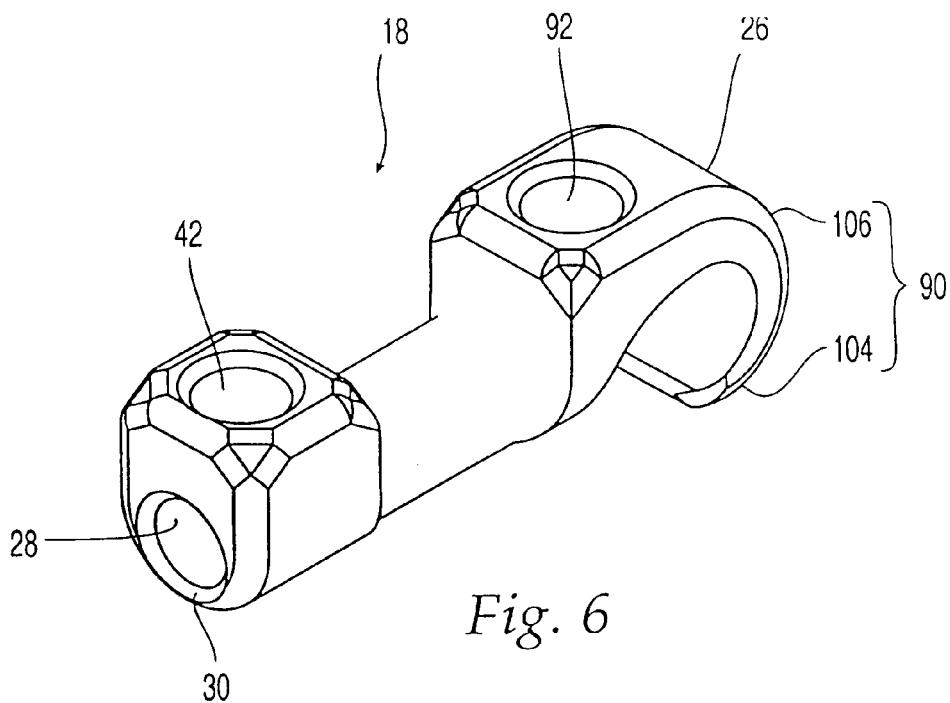
FIG. 6 shows a perspective view of the female member of the transconnector.
Figure 7:
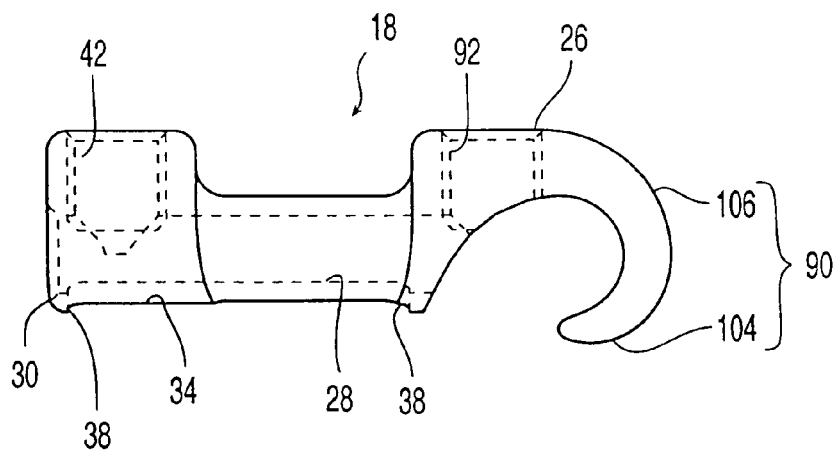
FIG. 7 shows a side view of the female member.

Transconnector 10 includes a male member 16, a female member 18, and a locking member 20. Male member 16 has a body with a linking element 22 on the lateral end for receiving first fixation element 12 and a projection 24 extending from the medial end of the body. Female member 18 has a body with a linking element 26 on the lateral end for receiving second fixation element 14 and a cavity 28 with an opening 30 (FIGS. 6 and 7) on the medial end of the body for receiving a portion of projection 24. Locking member 20 secures the portion of projection 24 in cavity 28. The portion of projection 24 received in cavity 28 is adjustable for accommodating different separation distances d between first and second fixation elements 12, 14. This feature allows transconnector 10 to be readily adjusted for different patient anatomies and used in different regions of the spine. For example, the lumbar vertebrae are typically larger than the thoracic vertebrae. As a result, the distance between fixation elements in the lumbar region would be greater than fixation elements in the thoracic region. Because the length of projection that slides into cavity 28 can be varied, transconnector can be adjusted for use in different spinal regions without the need to bend either fixation rods or transconnector 10. In order to further increase the adjustability of transconnector 10, female member 18, cavity 28, and projection 24 can be manufactured in different sizes.

Projection 24 is rotatable in cavity 28 for accommodating differences between the angular orientation of first fixation element 12 with respect to the coronal plane and the angular orientation of second fixation element 14 with respect to the coronal plane. Specifically, first fixation element 12 has a longitudinal axis $L_1$ which runs at an angle $ÿ_1$ with respect to Line $AP_1$, which is perpendicular to plane C, and second fixation element 14 has a longitudinal axis $L_2$ which runs at an angle $ÿ_2$ with respect to Line $AP_2$, which is also perpendicular to plane C, a plane which divides the body in half from front to back. Because projection 24 can rotate in cavity 28, transconnector can be used in situations in which $ÿ_1$ differs from $ÿ_2$ without the need to bend either fixation element or transconnector 10.

Figure 3:
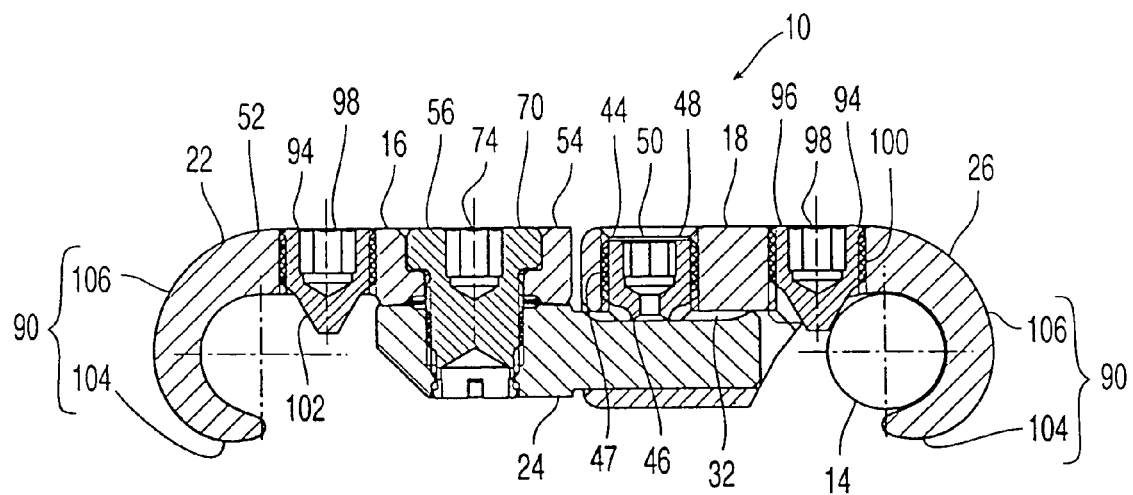
FIG. 3 shows a cross-sectional view of the transconnector with one fixation element attached.
Figure 5:
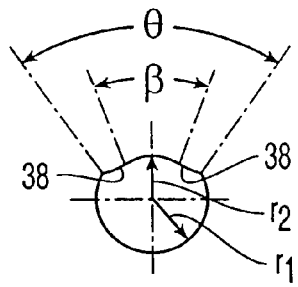
FIG. 5 shows a cross-section of the male member taken through line 5—5 of FIG. 4.
Figure 4:
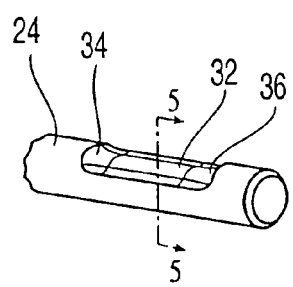
FIG. 4 shows a perspective view of a portion of one embodiment of the male member.
Figure 9:
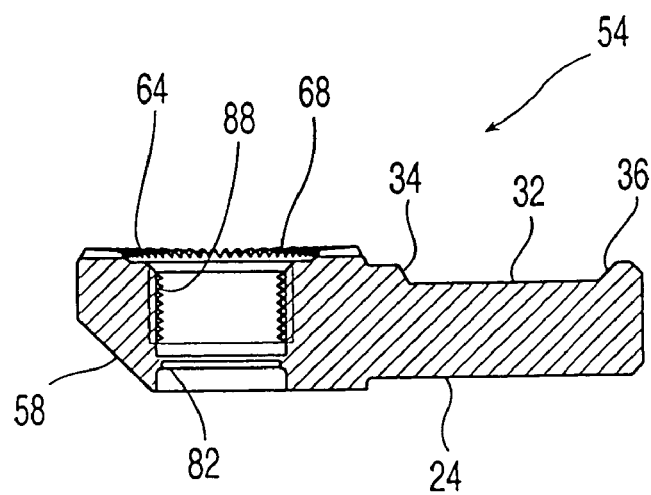
FIG. 9 shows a cross-sectional view of an intermediate link of the male member.
Figure 9A:
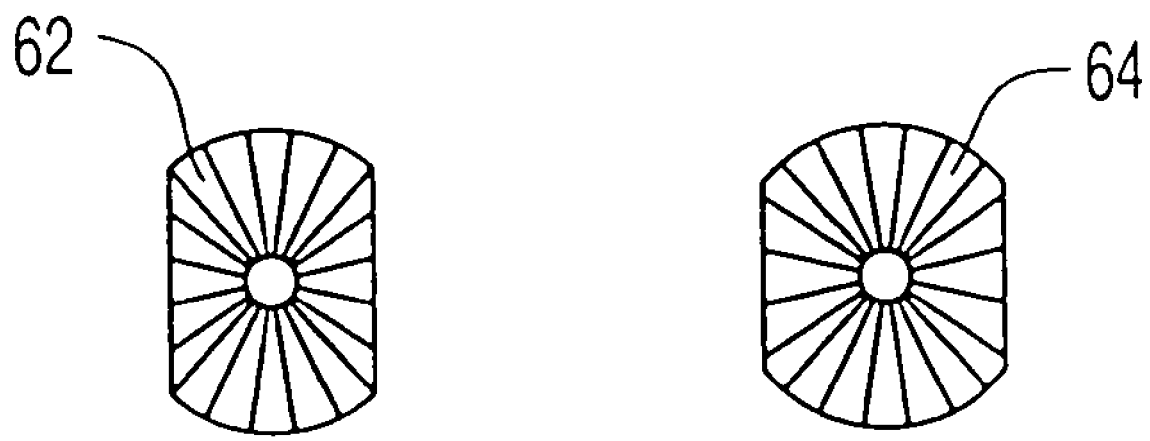
FIG. 9a shows a plan view of a textured surface of the link terminal and a textured surface of the intermediate link.

As seen best in FIGS. 3, 4, and 5, projection 24 has a substantially cylindrical-like shape and includes a recess 32 defined by lateral and medial walls 34, 36. As will be described in more detail below, medial wall 36 of recess 32 forms a stop against locking member 20 to limit travel of projection 24 in cavity 28, thereby preventing uncoupling of male member 16 and female member 18. Recess 32 can be formed having a number of different configurations (e.g. a flat planar surface) so long as medial wall 36 contacts locking member 20 before projection 24 is completely removed from cavity 28 and projection 24 can rotate within cavity 28. FIGS. 4, 5, and 9 show an exemplary embodiment of recess 32. A portion of an upper surface of recess 32, defined by angle $ÿ$, has a reduced radius $r_2$ compared to the radius $r_1$ outside of the area defined by angle $ÿ$. Arcuate surfaces 38 serve as a transition region from reduced radius $r_2$ to radius $r_1$. Radius $r_2$ and arcuate surfaces 38 can be manufactured using a number of different techniques. For example, they can be machined out by cutting, ball milling, or other milling processes.

As previously noted, locking member 20 secures the portion of projection 24 in cavity 28. FIGS. 1, 3, 6, and 7 show that locking member 20 includes a threaded hole 42 in female member 18 and a set screw 44. Set screw 44 threads into threaded hole 42 and a second end 46 presses projection 24 to clamp it against the walls of cavity 28. In an exemplary embodiment, set screw 44 comprises a threaded cylindrical body 47 that transitions to a tip at second end 46. A first end 48 of set screw 44 has an appropriately shaped and sized hole 50 (or a slot) for receiving a surgical instrument like a screwdriver to turn set screw 44.

As also previously noted, projection 24 can rotate in cavity 28 to accommodate different orientations of first and second fixations elements 12, 14. The degree of possible rotation is determined by the geometries of recess 32 and set screw 44. Specifically, projection 24 can rotate within recess 32 until set screw 44 engages the edges of recess 32. With respect to the embodiment shown in FIGS. 4 and 5, angle ÿ, which includes the area of angle ÿ and arcuate surfaces 38, defines the amount of rotation of projection 24 that is possible until second end 46 of set screw 44 engages the edges of recess 32 (that has the larger radius $r_1$).

In summary, recess 32 and locking member 20 interact to permit accommodation of non-coplanar rods and variability in rod separation distances. When locking member 20 includes set screw 44, set screw 44 can be in two basic positions. In the clamped position, set screw 44 is threaded into threaded hole 42 so that second end 46 presses against recess 32 to clamp projection 24 against the walls of cavity 28. In the un-clamped position, movement of projection 24 within cavity 28 is permitted. The range of movement is limited by contact between set screw 44 and the boundaries of recess 32. In one embodiment, set screw 44 can be completely removed from threaded hole 42, thereby allowing projection 24 to completely leave cavity 28 and complete uncoupling of male and female members 16, 18. In another embodiment, set screw 44 is "staked" so that set screw 44 can not come out of threaded hole 42 without an increase in torque. One way to achieve this is by mechanically deforming the first threads of threaded hole 42 so that set screw 44 cannot be unscrewed past the damaged threads. It should also be noted that depending on the relative geometries of the set screw 44 and medial wall 36, uncoupling of male and female members 16, 18 may still be possible even without complete removal of set screw 44 from threaded hole 42 regardless of whether set screw 44 is staked.

Figure 8:
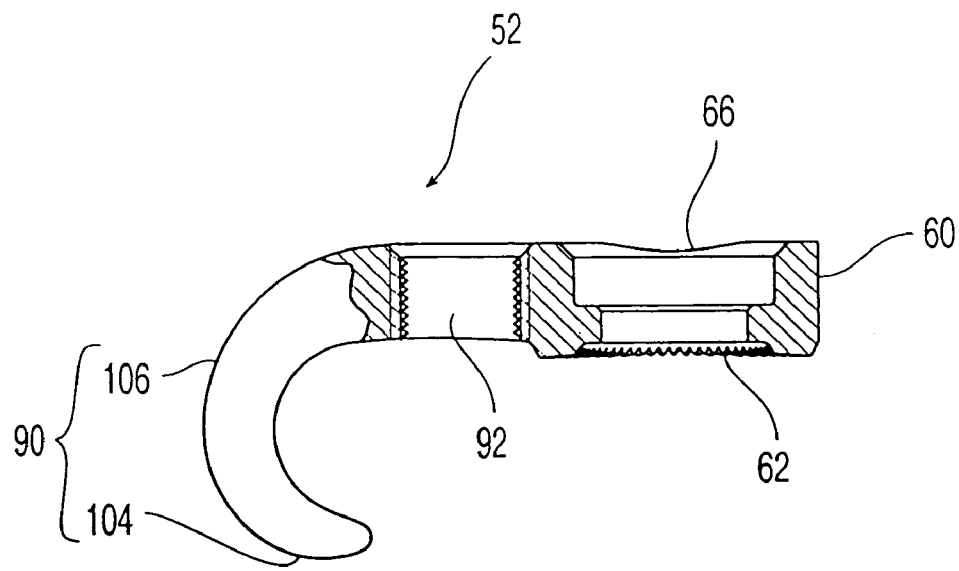
FIG. 8 shows a side view of a link terminal of the male member with a partial cross section.

FIGS. 1, 8, and 9 show an exemplary embodiment of the body of male member 16 as a two piece assembly which includes a link terminal 52, an intermediate link 54, and a locking element 56 to secure the two together. A lateral end of link terminal 52 has male member linking element 22 and intermediate link 54 has a medial end with projection 24 and a lateral end 58 which engages a medial end 60 of link terminal 52. Medial end 60 of link terminal 52 includes a first textured surface 62 which mates with a second textured surface 64 of lateral end 58 of intermediate link 54 in such a fashion that first textured surface 62 is rotatable with respect to second textured surface 64 to accommodate for any convergence or divergence between first and second fixation elements 12, 14. First and second textured surfaces 62, 64 are provided with a plurality of teeth, such as a radial or star-grind pattern, in order to help maintain link terminal 52 at the desired angular orientation. Locking element 56 includes a first hole 66 through medial end 60 of link terminal 52 and a second hole 68 through lateral end 58. First and second holes 66, 68 align so that a cap screw 70 can be inserted therethrough.

Figure 10:
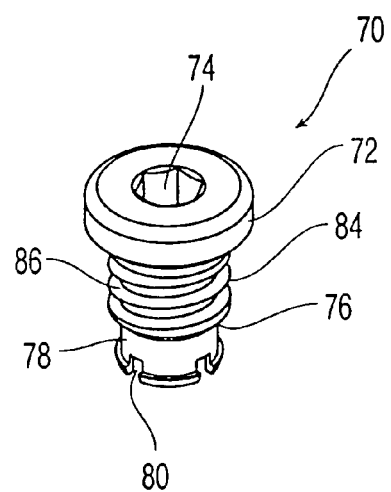
FIG. 10 shows a perspective view of a cap screw used to join the link terminal and intermediate link.

Referring to FIGS. 8–10, cap screw 70 has a first end 72 with a slot 74 for receiving a tool to turn cap screw 70 and a second end 76 with a retaining ring 78 for preventing removal of cap screw 70 from first and second holes 66, 68. Retaining ring 78 has slits 80 which allow retaining ring to flex inward to be inserted through a collar 82 in second hole 68. Once retaining ring 78 is inserted past collar 82, retaining ring 78 flexes back outward so that cap screw 70 can not be completely screwed out of first and second holes 66, 68. A body 84 of cap screw 70 is provided with threads 86 which engage threads 88 on the walls of second hole 68.

The structure of linking elements 22, 26 will depend on the structure of fixation elements 12, 14. For example, if fixation rods 12, 14 are elongate plates, then linking elements 22, 26 are configured and dimensioned to receive elongate plates. Such configurations and configurations for other types of fixation elements are well known in the art. If fixation elements 12, 14 are cylindrical rods as shown in the drawings, then linking elements 22, 26 each comprises a hook 90. The lateral ends of male and female members 16, 18 each includes a threaded hole 92 and a clamping screw 94 threadably received in threaded hole 92 for securing first and second fixation elements 12, 14 to hook 90.

Figure 2:
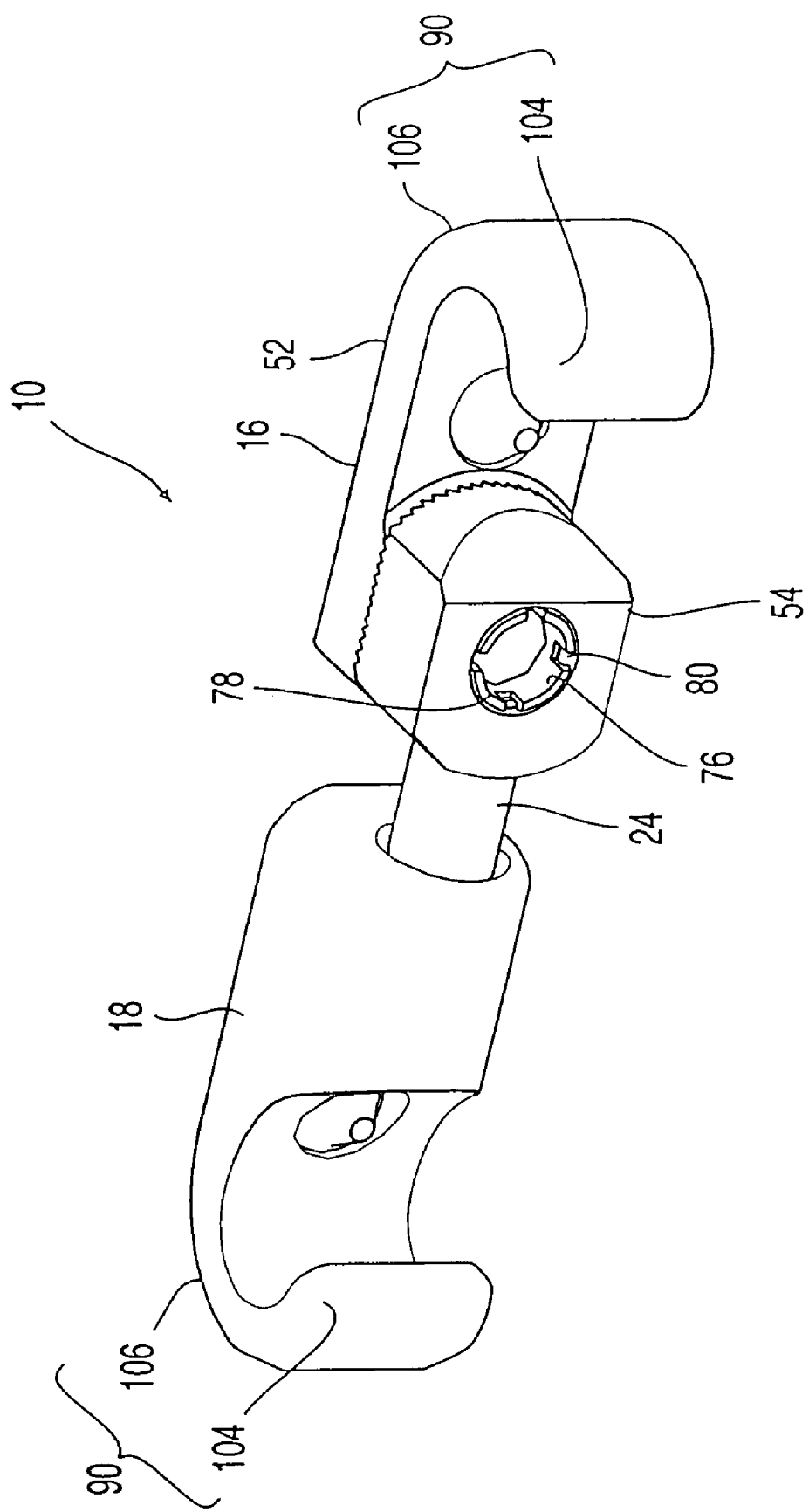
FIG. 2 shows a bottom perspective view of the transconnector without the fixation elements.

As seen best in FIGS. 2 and 3, each clamping screw 94 has a first end 96 with a slot 98 for receiving a tool to turn clamping screw 94, a threaded cylindrical first body portion 100, and a conical second body portion 102. Each hook 90 comprises a tip portion 104 and a curved portion 106. Curved portion 106 has a radius of curvature larger than the radius r of fixation elements 12, 14. As a result, the only contact between hooks 90 and fixation elements 12, 14 is at a region near tip portion 104. Furthermore, the only contact between clamping screws 94 and fixation elements 12, 14 is on conical second body portion 102. Thus, fixation elements 12, 14 is clamped between conical second body portion 102 and the region near tip portion 104.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A transconnector for coupling first and second longitudinal spinal rods, the transconnector comprising:
    a first member having a first hook portion sized and configured to engage the first longitudinal spinal rod and a projection associated with the first hook portion, the first hook portion having a through hole therein, and the projection having an aperture, the first member further comprising a shaft member extending through both the through hole and the aperture forming an axis of rotation about which the first hook portion can articulate with respect to the projection;

a second member having a second hook portion sized and configured to engage the second longitudinal spinal rod and a cavity having at least one opening sized and configured to receive at least a portion of the projection; and a locking assembly for securing different separation distances and angular orientation between the first and second members, the locking assembly having a first end accessible by a user to rotate at least a portion of the locking assembly to prevent at least one of the translational or rotational movement of the first member with respect to the second member;

wherein the locking assembly has at least a first position permitting the first member to slide and rotate with respect to the second member, with the first hook portion of the first member at a user selected angle relative to the second hook portion, and at least a second position preventing at least one of translational or rotational movement of the first member with respect to the second member.

2. The transconnector of claim 1 wherein rotation of the first end of the locking assembly presses the projection against the cavity.

3. The transconnector of claim 1 wherein a second end of the locking assembly directly or indirectly engages the projection to prevent movement of the first member with respect to the second member.

4. The transconnector of claim 1 wherein the locking assembly consists of a single screw.

5. The transconnector of claim 1 wherein the locking assembly is operatively associated with the projection to limit travel of the first member to prevent uncoupling of the first and second members.

6. The transconnector of claim 1 wherein the projection is an elongated member having an arcuate section with a relatively flat top surface and the flat top surface includes a medial wall.

7. The transconnector of claim 6 wherein the projection further includes side edges at respective junctures of the flat top surface and the arcuate section.

8. The transconnector of claim 7 wherein interaction of the locking assembly and the medial wall prevents uncoupling of the first and second members.

9. The transconnector of claim 8 wherein the side edges limit rotation of the projection in the cavity.

10. The transconnector of claim 9 wherein interaction of the locking assembly with the side edges limits rotation of the projection in the cavity.

11. The transconnector of claim 1 wherein the shaft member comprises a threaded screw.

12. The transconnector of claim 11 wherein the shaft member is adjustable to lock the hook portion of the first member with respect to the projection.

13. The transconnector of claim 1 wherein the projection comprises an edge formed by the junction between the arcuate portion and the flat surface, the edge and the cavity being sized and configured to limit angulation of the first member with respect to the second member.

14. The transconnector of claim 1 wherein at least a portion of the projection limits angulation of the first member with respect to the second member.

15. The transconnector of claim 1 wherein the locking assembly in the second position prevents both translational and rotational movement of the first member within respect to the second member.

16. The transconnector of claim 1 wherein the second member has a threaded opening sized and configured to threadedly receive the locking assembly.

17. The transconnector of claim 16 wherein the locking assembly comprises a set screw that directly or indirectly engages the projection to substantially prevent movement of the first member with respect to the second member.

18. The transconnector of claim 17 wherein the threaded opening has a central axis, the central axis is substantially perpendicular to the projection.

19. The transconnector of claim 1 wherein the cavity is integrally formed with the hook portion of the second member.

20. The transconnector of claim 1 wherein the first hook portion of the first member is integrally formed with the projection.

21. A transconnector for coupling first and second longitudinal spinal rods, the transconnector comprising:

a first member having a first hook portion sized and configured to engage the first longitudinal spinal rod and a projection associated with the first hook portion, the first member comprising:
  a first body portion having a lateral end incorporating the first hook portion and a medial end;
  a second body portion having a medial end incorporating the projection and a lateral end engaging the medial end of the first body portion; and
  a locking element for securing the first body portion with respect to the second body portion;

a second member having a second hook portion sized and configured to engage the second longitudinal spinal rod and a cavity having at least one opening sized and configured to receive at least a portion of the projection; and a locking assembly for securing different separation distances and angular orientation between the first and second members, the locking assembly having a first end accessible by a user to rotate at least a portion of the locking assembly to prevent at least one of the translational or rotational movement of the first member with respect to the second member;

wherein the locking assembly has at least a first position permitting the first member to slide and rotate with respect to the second member, with the first hook portion of the first member at a user selected angle relative to the second hook portion, and at least a second position preventing at least one of translational or rotational movement of the first member with respect to the second member.

22. The transconnector of claim 21 wherein the medial end of the first body portion includes a first textured surface; the lateral end of the second body portion includes a second textured surface mating with the first textured surface; and the first textured surface is rotatable with respect to the second textured surface for accommodating convergence or divergence between the first and second members.

23. The transconnector of claim 22 wherein the first and second textured surfaces include a star-grind pattern.

24. The transconnector of claim 23 wherein the locking element comprises:
  a first hole through the medial end of the first body portion;
  a second hole through the lateral end of the second body portion aligned with the first hole; and
  a cap screw insertable in the first and second holes.

25. The transconnector of claim 24 wherein the cap screw has a first end for receiving a tool to turn the cap screw and a second end with a retaining ring for preventing removal of the cap screw from the second hole.

26. The transconnector of claim 25 wherein the cap screw has a body with threads and the second hole is threaded for threadably receiving the cap screw.

27. The transconnector of claim 26 wherein the second hole includes a collar and the retaining ring includes a resilient member, the resilient member flexing inward upon insertion of the cap screw through the second hole and flexing outward once the resilient member is past the collar for preventing removal of the cap screw.

28. The transconnector of claim 27 wherein the resilient member includes an end of the cap screw with a lip and a plurality of slits.

29. The transconnector of claim 1 wherein the first hook portion of the first member and the second hook portion of the second member each includes a threaded hole and a clamping screw threadably received in the respective threaded hole for securing the first and second longitudinal spinal rods to the first and second members, respectively.

30. The transconnector of claim 29 wherein each clamping screw has a first end for receiving a tool to turn the clamping screw, a threaded cylindrical first body portion, and a conical second body portion.

31. The transconnector of claim 30 wherein the first hook portion of the first member and the second hook portion of the second member each comprises a tip portion and a curved portion having a radius of curvature larger than that of the first and second spinal longitudinal spinal rods, respectively.

32. The transconnector of claim 31 wherein the first and second longitudinal spinal rods are clamped between the conical second body portion of each clamping screw and a region near the tip portion of the first and second hook portion, respectively.

33. A transconnector for coupling first and second elongate spinal fixation elements, the transconnector comprising:
   a first member having a first linking portion configured and dimensioned to receive at least one of the elongate spinal fixation elements, and a projection associated with the first linking portion, the first linking portion having a through hole therein, and the projection having an aperture, the first member further comprising a shaft member extending through both the through hole and the aperture forming an axis of rotation about which the first linking portion can articulate with respect to the projection;
   a second member having a second linking portion configured and dimensioned to receive at least one of the elongate spinal fixation elements, and a cavity having at least one opening to receive at least a portion of the projection; and
   a locking assembly for securing different separation distances between the first and second fixation elements, the locking assembly having a first end accessible by a user to rotate at least a portion of the locking assembly to limit translational travel of the first member with respect to the second member,
   wherein the locking assembly has at least a first position permitting the first member to slide with respect to the second member, with the first linking portion of the first member at a user selected angle relative to the second linking portion of the second member, and at least a second position preventing translational movement of the first member with respect to the second member.

34. The transconnector of claim 33 wherein rotation of the first end of the locking assembly presses the projection against the cavity.

35. The transconnector of claim 33 wherein a second end of the locking assembly directly or indirectly engages the projection to prevent movement of the first member with respect to the second member.

36. The transconnector of claim 33 wherein the locking assembly consists of a single screw.

37. The transconnector of claim 33 wherein the locking assembly is operatively associated with the projection to limit travel of the first member to prevent uncoupling of the first and second members.

38. The transconnector of claim 33 wherein the projection has an arcuate portion with a relatively flat planar surface defining edges at the juncture of the flat planar surface and the arcuate portion and the flat planar surface includes a medial wall.

39. The transconnector of claim 38 wherein interaction of the locking assembly and the medial wall prevents uncoupling of the first and second members.

40. The transconnector of claim 39 wherein the edges limit rotation of the projection in the cavity.

41. The transconnector of claim 40 wherein interaction of the locking assembly with the side edges limits rotation of the projection in the cavity.

42. The transconnector of claim 33 wherein the shaft member comprises a threaded screw.

43. The transconnector of claim 42 wherein the shaft member is adjustable to lock the first linking portion of the first member with respect to the projection.

44. The transconnector of claim 33 wherein the edges and the cavity are sized and configured to limit angulation of the first member with respect to the second member.

45. The transconnector of claim 33 wherein at least a portion of the projection limits angulation of the first member with respect to the second member.

46. The transconnector of claim 33 wherein the second member has a threaded opening sized and configured to threadedly receive the locking assembly.

47. The transconnector of claim 46 wherein the locking assembly comprises a set screw that directly or indirectly engages the projection to substantially prevent movement of the first member with respect to the second member.

48. The transconnector of claim 47 wherein the threaded opening has a central axis, the central axis is substantially perpendicular to the projection.

49. The transconnector of claim 33 wherein the cavity is integrally formed with the second linking portion of the second member.

50. The transconnector of claim 33 wherein the first linking portion of the first member is integrally formed with the projection.

51. A transconnector for coupling first and second elongate spinal fixation elements, the transconnector comprising:
   a first member having a first linking portion configured and dimensioned to receive at least one of the elongate spinal fixation elements, and a projection associated with the first linking portion, the first member comprising:
      a first body portion having a lateral end incorporating the first linking portion and a medial end;
      a second body portion having a medial end incorporating the projection and a lateral end engaging the medial end of the first body portion; and
      a locking element for securing the first body portion with respect to the second body portion;

a second member having a second linking portion configured and dimensioned to receive at least one of the elongate spinal fixation elements, and a cavity having at least one opening to receive at least a portion of the projection; and a locking assembly for securing different separation distances between the first and second elongate spinal fixation elements, the locking assembly having a first end accessible by a user to rotate at least a portion of the locking assembly to limit translational travel of the first member with respect to the second member, wherein the locking assembly has at least a first position permitting the first member to slide with respect to the second member, with the first linking portion of the first member at a user selected angle relative to the second linking portion of the second member, and at least a second position preventing translational movement of the first member with respect to the second member.

52. The transconnector of claim 51 wherein the medial end of the first body portion includes a first textured surface; the lateral end of the second body portion includes a second textured surface mating with the first textured surface; and the first textured surface is rotatable with respect to the second textured surface for accommodating convergence or divergence between the first and second members.

53. The transconnector of claim 52 wherein the first and second textured surfaces include a star-grind pattern.

54. The transconnector of claim 51 wherein the locking element comprises:
    a first hole through the medial end of the first body portion;
    a second hole through the lateral end of the second body portion aligned with the first hole; and
    a cap screw insertable in the first and second holes.

55. The transconnector of claim 54 wherein the cap screw has a first end for receiving a tool to turn the cap screw and a second end with a retaining ring for preventing removal of the cap screw from the second hole.

56. The transconnector of claim 55 wherein the cap screw has a body with threads and the second hole is threaded for threadably receiving the cap screw.

57. The transconnector of claim 56 wherein the second hole includes a collar and the retaining ring includes a resilient member, the resilient member flexing inward upon insertion of the cap screw through the second hole and flexing outward once the resilient member is past the collar for preventing removal of the cap screw.

58. The transconnector of claim 57 wherein the resilient member includes an end of the cap screw with a lip and a plurality of slits.

59. The transconnector of claim 33 wherein the first linking portion of the first member and the second linking portion of the second member each includes a threaded hole and a clamping screw threadably received in the respective threaded hole for securing the first and second elongate spinal fixation elements to the first and second members, respectively.

60. The transconnector of claim 59 wherein each clamping screw has a first end for receiving a tool to turn the clamping screw, a threaded cylindrical first body portion, and a conical second body portion.

61. The transconnector of claim 60 wherein the first linking portion of the first member and the second linking portion of the second member each comprises a tip portion and a curved portion having a radius of curvature larger than that of the first and second elongate spinal fixation elements, respectively.

62. The transconnector of claim 61 wherein the first and second elongate spinal fixation elements are clamped between the conical second body portion of each clamping screw and a region near the tip portion of the first and second linking portions, respectively.

63. A transconnector for coupling first and second longitudinal spinal rods, the transconnector comprising:
    a first member having a first hook portion sized and configured to engage the first longitudinal spinal rod and a projection associated with the first hook portion, the first hook portion having a through hole therein, and the projection having an aperture, the first member further comprising a shaft member extending through both the through hole and the aperture forming an axis of rotation about which the hook portion can articulate with respect to the projection;
    a second member having a second hook portion sized and configured to engage the second longitudinal spinal rod and a cavity having at least one opening sized and configured to receive at least a portion of the projection; and
    a locking assembly for securing different separation distances and angular orientation between the first and second members, the locking assembly having a first end and a second end, the first end being accessible to a user so that rotation of the first end of the locking assembly causes the second end of the locking assembly to directly or indirectly engage the projection;
    wherein rotation of the first end of the locking assembly further moves the transconnector from a first position to a second position, the first position permitting the first member to slide and rotate with respect to the second member, with the first hook portion of the first member at a user selected angle relative to the second hook portion of the second member, the second position preventing at least one of translational or rotational movement of the first member with respect to the second member.

64. The transconnector of claim 63 wherein rotation of the first end of the locking assembly presses the projection against the cavity.

65. The transconnector of claim 63 wherein the locking assembly consists of a single screw.

66. The transconnector of claim 63 wherein the locking assembly is operatively associated with the projection to limit travel of the first member to prevent uncoupling of the first and second members.

67. The transconnector of claim 63 wherein the projection is an elongated member having an arcuate portion with at least one relatively flat surface and the flat surface includes a medial wall.

68. The transconnector of claim 67 wherein the projection further includes side edges at the juncture of the flat surface and the arcuate portion.

69. The transconnector of claim 68 wherein interaction of the locking assembly and the medial wall prevents uncoupling of the first and second members.

70. The transconnector of claim 69 wherein the side edges limit rotation of the projection in the cavity.

71. The transconnector of claim 70 wherein interaction of the locking assembly with the side edges limits rotation of the projection in the cavity.

72. The transconnector of claim 63 wherein the shaft member comprises a threaded screw.

73. The transconnector of claim 63 wherein the shaft member is adjustable to lock the hook portion of the first member with respect to the projection.

74. The transconnector of claim 63 wherein the projection comprises an edge formed by the junction between the arcuate portion and the flat surface, the edge and the cavity being sized and configured to limit angulation of the first member with respect to the second member.

75. The transconnector of claim 63 wherein at least a portion of the projection limits angulation of the first member with respect to the second member.

76. The transconnector of claim 63 wherein the locking assembly in the second position prevents both translational and rotational movement of the first member within respect to the second member.

77. The transconnector of claim 63 wherein the second member has a threaded opening sized and configured to threadedly receive the locking assembly.

78. The transconnector of claim 77 wherein the locking assembly comprises a set screw that directly or indirectly engages the projection to substantially prevent movement of the first member with respect to the second movement.

79. The transconnector of claim 78 wherein the threaded opening has a central axis, the central axis is substantially perpendicular to the projection.

80. The transconnector of claim 63 wherein the cavity is integrally formed with the hook portion of the second member.

81. The transconnector of claim 63 wherein the first hook portion of the first member is integrally formed with the projection.

82. A transconnector for coupling first and second longitudinal spinal rods, the transconnector comprising:
 a first member having a first hook portion sized and configured to engage the first longitudinal spinal rod and a projection associated with the first hook portion, the first member comprising:
  a first body portion having a lateral end incorporating the first hook portion of the first member and a medial end;
  a second body portion having a medial end incorporating the projection of the first member and a lateral end engaging the medial end of the first body portion; and
  a locking element for securing the first body portion with respect to the second body portion;
 a second member having a second hook portion sized and configured to engage the second longitudinal spinal rod and a cavity having at least one opening sized and configured to receive at least a portion of the projection; and
 a locking assembly for securing different separation distances and angular orientation between the first and second members, the locking assembly having a first end and a second end, the first end being accessible to a user so that rotation of the first end of the locking assembly causes the second end of the locking assembly to directly or indirectly engage the projection;
 wherein rotation of the first end of the locking assembly further moves the transconnector from a first position to a second position, the first position permitting the first member to slide and rotate with respect to the second member, with the first hook portion of the first member at a user selected angle relative to the second hook portion of the second member, the second position preventing at least one of translational or rotational movement of the first member with respect to the second member.

83. The transconnector of claim 82 wherein the medial end of the first body portion includes a first textured surface; the lateral end of the second body portion includes a second textured surface mating with the first textured surface; and the first textured surface is rotatable with respect to the second textured surface for accommodating convergence or divergence between the first and second members.

84. The transconnector of claim 83 wherein the first and second textured surfaces include a star-grind pattern.

85. The transconnector of claim 82 wherein the locking element comprises:
 a first hole through the medial end of the first body portion;
 a second hole through the lateral end of the second body portion aligned with the first hole; and
 a cap screw insertable in the first and second holes.

86. The transconnector of claim 85 wherein the cap screw has a first end for receiving a tool to turn the cap screw and a second end with a retaining ring for preventing removal of the cap screw from the second hole.

87. The transconnector of claim 86 wherein the cap screw has a body with threads and the second hole is threaded for threadably receiving the cap screw.

88. The transconnector of claim 87 wherein the second hole includes a collar and the retaining ring includes a resilient member, the resilient member flexing inward upon insertion of the cap screw through the second hole and flexing outward once the resilient member is past the collar for preventing removal of the cap screw.

89. The transconnector of claim 88 wherein the resilient member includes an end of the cap screw with a lip and a plurality of slits.

90. The transconnector of claim 63 wherein the first hook portion of the first member and the second hook portion of the second member each includes a threaded hole and a clamping screw threadably received in the respective threaded hole for securing the first and second longitudinal rods to the first and second members, respectively.

91. The transconnector of claim 90 wherein each clamping screw has a first end for receiving a tool to turn the clamping screw, a threaded cylindrical first body portion, and a conical second body portion.

92. The transconnector of claim 91 wherein the first hook portion of the first member and the second hook portion of the second member each comprises a tip portion and a curved portion having a radius of curvature larger than that of the first and second longitudinal rods, respectively.

93. The transconnector of claim 92 wherein the first and second longitudinal rods are clamped between the conical second body portion of each clamping screw and a region near the tip portion of the first and second hook portion, respectively.

* * * * *